(12) United States Patent
Bredehorst et al.

(10) Patent No.: US 6,881,379 B1
(45) Date of Patent: Apr. 19, 2005

(54) METHOD FOR PRODUCING DETECTION SYSTEMS WITH PLANAR ARRAYS

(75) Inventors: Reinhard Bredehorst, Hamburg (DE); Rainer Hintsche, Berlin (DE); Rene Seitz, Itzehoe (DE); Walter Gumbrecht, Herzogenaurach (DE)

(73) Assignee: Fraunhofer-Gesellschaft zur Foerderung der Angewandten Forschung e.V., Munich (DE)

( * ) Notice: Subject to any disclaimer, the term of this patent is extended or adjusted under 35 U.S.C. 154(b) by 0 days.

(21) Appl. No.: 09/958,807
(22) PCT Filed: Apr. 14, 2000
(86) PCT No.: PCT/EP00/03398
§ 371 (c)(1), (2), (4) Date: Dec. 11, 2001
(87) PCT Pub. No.: WO00/67026
PCT Pub. Date: Nov. 9, 2000

(30) Foreign Application Priority Data

Apr. 14, 1999 (DE) ......................................... 199 16 867

(51) Int. Cl.[7] ............................................... G01N 33/50
(52) U.S. Cl. ............................. 422/58; 422/56; 422/57; 422/82.01; 422/82.02; 422/82.03; 422/82.04; 422/82.05; 422/82.06; 422/82.07; 422/82.08; 422/82.09; 436/166; 436/169; 436/518; 436/524; 436/527; 436/528
(58) Field of Search ............... 422/56–58, 82.01–82.09, 422/102; 436/166, 169, 518, 524, 525, 527, 528, 531, 532

(56) References Cited

U.S. PATENT DOCUMENTS 5,143,854 A * 9/1992 Pirrung et al. ............... 436/518
5,474,796 A * 12/1995 Brennan ..................... 427/2.13
5,605,662 A    2/1997 Heller et al. ................ 422/68.1

(Continued)

FOREIGN PATENT DOCUMENTS

DE    197 06 570      2/1998
DE    196 46 505      5/1998
WO    WO 98/23957    6/1998

OTHER PUBLICATIONS

McGall, g. et al, Proceedings of the National Academy of Science, USA 1996, 93, 13555–13560.*
Case–Green, S. C. et al, Current Opinion in Chemical Biology 1998, 2, 404–410.*
Bidan, G. et al., "Conducting Polymers as a Link Between Biomolecules and Microelectronics", Synthetic Metals (1999), vol. 102, pp. 1363–1365, Elsevier Science S.A.
Wadkins et al., "Detection of Multiple Toxid Agents Using a Planar Array Immunosensor", Biosensors & Bioelectronics, vol. 13, 1998, pp. 407–415.

*Primary Examiner*—Arlen Soderquist
(74) *Attorney, Agent, or Firm*—Foley & Lardner LLP

(57) ABSTRACT

The invention relates to a method for producing a detection system for detecting different analytes in a sample, characterised by the following steps: providing a planar or essentially planar substrate which has sensors for chemically, optically or electrically detecting the analytes; applying an already microstructured layer to the substrate or applying a continuous layer to the substrate and microstructuring said layer, the layer being applied in such a way in either case that the areas of the substrate that are separated from each other are not covered by the layer, the layer and substrate being sealingly interconnected at least around the uncovered areas; bringing at least some of the uncovered areas into contact with at least one liquid containing catcher molecules, in such a way that said catcher molecules are able to adhere or bond to the surface of the substrate and/or on the surface of the sensors; removing the non-adhering constituents of the liquid and removing the microstructured layer or parts thereof.

45 Claims, 4 Drawing Sheets

U.S. PATENT DOCUMENTS

| | | | |
|---|---|---|---|
| 5,653,939 A | 8/1997 | Hollis et al. | 422/50 |
| 5,812,272 A * | 9/1998 | King et al. | 356/445 |
| 5,827,748 A * | 10/1998 | Golden | 436/527 |
| 6,228,326 B1 * | 5/2001 | Boxer et al. | 422/82.02 |
| 6,395,483 B1 * | 5/2002 | Patil et al. | 435/6 |
| 6,406,921 B1 * | 6/2002 | Wagner et al. | 436/518 |
| 6,653,151 B1 * | 11/2003 | Anderson et al. | 436/518 |

\* cited by examiner

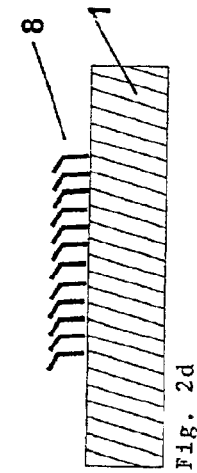
Fig. 2d
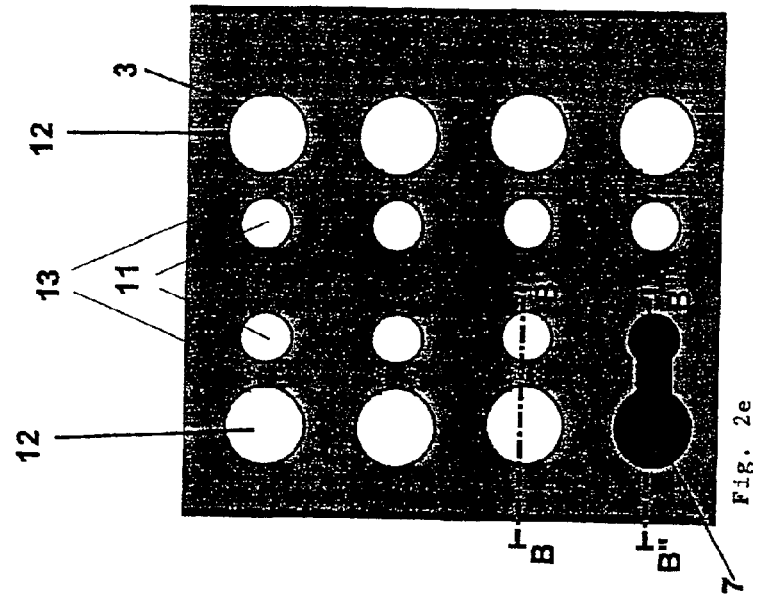
Fig. 2e
FIG. 2
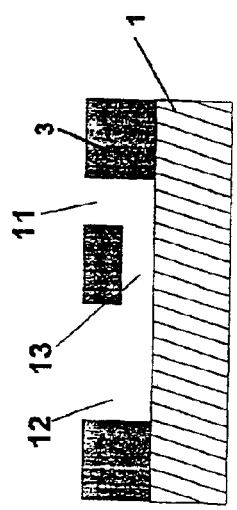
Fig. 2a
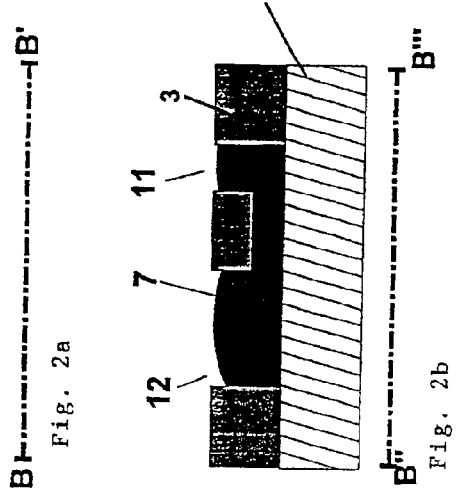
Fig. 2b
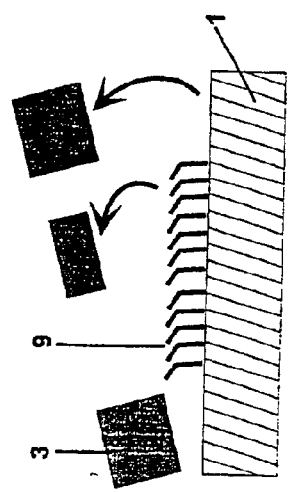
Fig. 2c

METHOD FOR PRODUCING DETECTION SYSTEMS WITH PLANAR ARRAYS

This is a National Stage Application of PCT/EP00/03398, filed Apr. 14, 2000.

The invention relates to a fabrication of planar substrates or planar sensor elements on which identical or different biomolecules are arranged in immobilized form, areally delimited with respect to one another, as so-called arrays. This arrangement is preferentially employed as part of measuring devices in chemical analysis, biotechnology and industrial process control. The invention also relates to substrates or sensor elements in which a planar substrate having a specifically patterned layer or ply is partially covered in such a way that specifically shaped microcompartments are formed in which the biomolecules can be immobilized on the bare substrate surface. Said specifically patterned layer or ply can be removed again, if required, from the substrate, resulting in the abovementioned planar substrate or sensor elements.

For the purpose of immobilizing and locating various types of chemical species in small, local areas, microreactors, microcompartments or microcavities have long been known, which are fabricated in silicon and glass means of standard procedures of microsystem technology, e.g. as etched patterns in Si- or glass-microsystem technology and in plastics via embossing procedures. Also known is a photolithographic technique for producing tiny separated microactivities in polystyrene. The etched ends of fiber bundles embedded in polymers have likewise previously been utilized as microcavities.

U.S. Pat. No. 5,605,662 describes the formation of micropatterned areas which are surrounded by walls of the substrate and comprise gel-covered electrodes for absorbing various molecules, e.g. nucleotides, and expands charging with liquids.

Characteristic drawbacks of the abovedescribed permanent microcavities or compartment patterns, which as a rule have a simple geometry (angular or round "depressions") for fabricating bioarrays are the existing mechanical obstacles on the surface of the substrate. The necessary even supply of the agents and purging operations cannot readily be implemented in microcavities, since high capillary forces can impede the liquid exchange and thus, in the event of successive reaction steps, cause unwanted contamination. Moreover, filling of the microcavities is impeded, particularly with Si and glass surfaces, by the formation of air bubbles. Technological difficulties and disadvantages in terms of cost arise in particular in those cases where it is necessary for chemical or physical sensor elements to be individually placed within or underneath the microcavities. A further drawback of the permanently volume-compartmented microarrays having the above-mentioned simple geometry is the difficulty of distributing analytes homogeneously and uniformly into all the microcompartments and, where necessary, remove them again therefrom in a similar manner.

In Science 264 (1994) 696, R. Shighvi et al. described an elastomeric polysiloxane stamp for molding by means of photolithographic techniques, said stamp being suitable for producing molecularly patterned arrays by means of printing and abstraction processes by means of thiol-derivatized fatty acids. As a result of this stamp being stamped onto gold substrates, self-organized monomolecular layers matching the shape of the stamp are able to form, which can be utilized as a barrier for growing cells. A further development of this technology, also referred to as microcontact printing, is described in Nanotechnology 7 (1996) 452. There, gold surfaces can be coated with monomolecular layers by means of a stamp and be utilized as a protection against chemical etching away, to allow substrate regions situated between the stamp areas to be patterned down into the nm range. Additionally, areas in the silicon or glass which are then freed of gold and metal can be etched chemically, thus allowing micromechanically produced depressions or microcompartments having geometries between a few nm and several $\mu$m to be fabricated. A further variant offset microcontact printing is described in combination with dry etching processes [Nanotechnology 7 (1996) 447].

A procedure derived from macroscopic dabbing on is that of putting down miniaturized rings onto chipped surfaces to which matching molecules had previously been applied by dipping [S. D. Rose, J. Ass. Lab. Autom. 3,3 (1998) 53]. The risk of contamination with this method is considerable.

So-called microcontact printing, i.e. the transfer of molecules by means of microstamps, was described by A. Kumar and G. M. Whitesidess (Appl. Phys. Lett. 63 (1993) 2002].

Drawbacks of the stamp techniques include inadequate edge precision and inhomogeneities in the areal distribution of the molecules, particularly as the stamp area increases.

Localized substance arrays can also be produced by using a micro-misting technique. The localized application of extremely small microscopic particles of liquids comprising various substances is also possible onto patterned, so-called "selfassembled monolayers". Filling with micro-droplets in the way of the generally known inkjet printing techniques is likewise possible and is often used; analogous inkjet technology is also used to deposit so-called microspots onto planar substrates and transducers.

So-called microcontact printing, i.e. the transfer of molecules by means of microstamps, was described by A. Kumar and G. M. Whitesidess (Appl. Phys. Lett. 63 (1993) 2002].

To generate planar arrays comprising different immobilized molecules, Blanchard et al., Biosensors & Bioelectronics 11 (1996) 687, describes the deposition of droplets of liquid by means of inkjet printing technology onto circular areas of a size of about 100 $\mu$m and having hydrophilic surface characteristics, which are separated by regions about 30 $\mu$m wide having hydrophobic surface characteristics. Owing to the poorer wetability of the hydrophobic regions with biaqueous liquids, mixing of adjacent droplets is to be prevented. Since hydrophilic and hydrophobic regions do not differ in altitude, the risk of mechanically produced contamination remains, particularly with the rapid, automated application methods, thereby restricting applicability of the method.

The procedures described for generating arrays on planar elements by means of the above-mentioned microspot, misting or printing methods require rapid drying of the liquids and reactants used, to prevent mixing. Problems of these procedures are geometric irregularities of the spots, the impossibility of quantitative dosing at individual positions, and the limitations of the applicable coupling reactions in liquid phase and the possible carry-over of substances between individual array positions.

A further procedure for pattern covering of surfaces is photochemically induced binding of molecules or molecular chains to laser-activated microsurfaces [A. C. Pease et al., Proc. Natl. Acad. Sci., USA 91 (1994), 5022]. Organic bonding layers and coupling layers can also be applied selectively with the aid of electropolymerization, for example to bind ferrocenes to platinum electrodes.

A more recent method of producing and filling microcavities in nm and μm dimensions is the so-called "dewetting" technique, which utilizes capillary forces for filling and makes use of the liquid flowing off the planar surface [Whitesides et al., Anal. Chem. 70 (1998) 2280].

Perforated membranes, which are pressed onto chipped surfaces with the aid of a stamp, at their open positions allow immobilization reactions at the surfaces in liquid phase [E. Ermantraut et al., Proc. of μTAS'98, Alberta, Can., 1998, p. 217]. This method holds contamination problems due to capillary forces between stamp and a raised surface, resulting in possible errors during synthesis or immobilization reactions.

R. M. Wadkins et al., Biosensors & Bioelectronics 13 (1998) 407, temporarily produced microcompartments having a height of 0.2 mm by photopatterning of a liquid polymer adhesive. After photopatterning, adhesive which had not crosslinked was removed again manually by means of an acetone-soaked wad of cotton wool. Conventional immobilization methods were then used to bind various antibodies to the bottom of the compartments. Later, the compartments were removed again by stripping with protein-salt solution. Determination of the analyte was carried out by irradiating the immobilized sample with a laser, reflected light being analyzed after it had passed through optical systems (gratings, filter).

Because of its manual steps, the procedure proposed by Wadkins et al. is unsuitable for a mass production using industrial standard methods, e.g. on wafers. Another drawback is that the output signal taken off the sample cannot be captured directly at the immobilization site.

An assessment of the bioarray construction methods described shows that there is a need for optimization in terms of technologically compatible and efficient dosing methods without contamination problems in conjunction with convenient handling of the finished array in liquids.

The modification and coverage of inorganic surfaces with monomeric and especially with polymeric bimolecules is performed in various ways in the prior art, said bimolecules being applied as a single layer or as a multilayer, e.g. by covalent binding, adsorption, intercalation into polymers or as crystalline films.

For chemical binding, the inorganic surfaces of the base substrates are treated e.g. with bifunctional reagents, in order to provide the surfaces with chemical functions which are able to react with biomolecules. Subsequent binding of the biomolecules through the derivatized surface can either take place directly or alternatively indirectly, making use of further homo- or hetero-bifunctional molecules [C. F. Mandenius et al., Methods in Enzymology 137 (1988) 388].

A widely used approach is to generate bonding layers on surfaces by means of functionalized silanes as monolayers [C. M. Fischer et al., Europhysics Letters 28 (2) (1994) 129–134] or via transversely crosslinked layers applied from the gas state or in liquid phase [R. A. Williams et al., Biosensors & Bioelectronics 9 (1994) 159]. Covalently bound to these silane derivatives, which can carry amino, thiol, aldehyde, hydroxyl, carboxyl or other functional groups, are a great variety of other compounds having suitable reactive groups, usually with the aid of crosslinking techniques [H. G. Baumert and H. Fasold, Methods in Enzymology, Vol. 172, p. 584]. Thus, all bioactive substances suitable as affinity-binding capturing molecules, such as oligonucleotides, peptides, haptenes and the like can be immobilized on the electrode surfaces.

The methods listed represent standard methods which permit DNA, oligonucleotides, proteins and other molecules to be immobilized on array positions.

It is an object of the present invention to provide a method which permits bioarrays to be formed on planar substrates, said bioarrays comprising capturing molecules adhering to the substrate surface ("detection systems"), and which is technologically simple and/or compatible with microelectronic chip fabrication. The substrates or biosensors thus fabricated, shall, in a wafer assembly, enable immobilization of biomolecules, minimize contamination problems and be homogeneously accessible and without problems in terms of fluidic operation. The method shall lead to substrates or biosensors ("detection systems") with the aid of which it will be possible, very compactly, either to test a multiplicity of samples for the presence of one substance to be detected ("analyte") or one sample for the presence of a multiplicity of substances ("analytes").

In special embodiments of the invention it is a further object, making use of the said method, to provide intermediary embodiments of the detection systems which owing to geometric conditions have specific advantages.

According to the invention, the object is achieved by a method of fabricating a detection system for detecting various analytes in one sample or for detecting one analyte in a multiplicity of samples, the detection system comprising a planar or essentially planar substrate surface and, arranged on said plane, arrays of analyte-binding capturing molecules, characterized by the following steps;

(a) providing a planar or essentially planar substrate with sensors for the chemical, optical or electrical detection, (b) applying a layer to the substrate, said layer being either already micropatterned or applying a continuous layer to the substrate and micropatterning the layer, in each case in such a way that disjunct regions of the substrate are not covered by the layer, where layer and substrate are sealingly joined to one another at least around the uncovered regions, (c) bringing at least part of the uncovered regions into contact with at least one liquid which contains capturing molecules, in such a way that the capturing molecules are capable of adhering to the substrate surface and/or to the surface of the sensors or to bind thereto, (d) removing the non-adhering constituents of the liquid, (e) removing the micropatterned layer or parts of said layer.

The disjunct regions of the substrate, which are not covered by the layer, can also be referred to as microcompartments. In step (b) such microcompartments are formed which, because of those portions of the layer which surround them, have a lateral boundary, i.e. are separated from one another by mechanical barriers. This boundary or barrier is eliminated again by step. (e), which means that after this step the microcompartments in the form of regions which are occupied by capturing molecules and which are also referred to as (bio)arrays, are disposed without a lateral boundary on the substrate surface or the surface of the sensors.

The term "capturing molecules" refers to those substances which can be immobilized on the surface of the substrate and/or the sensors, without any restriction regarding the immobilization method; those skilled in the art here have a wide range of options at their disposal, some of which were mentioned in the introduction to this application. The immobilization can be effected by chemical binding or by adhesion or the like; it can be effected directly or with the aid of further substances by means of which suitable chemical groups are provided on the substrate surface or sensor surface. The term "capturing molecules" is further meant to indicate that these substances have suitable groups so as to keep the analytes close to them, either directly or by involving further substances. In the process, the analyte can be chemically or physically "captured" or bound; in addition to a chemical bond, therefore, Van der Waals bonds, adhesion or the like can cause the analyte to remain close to the capturing molecules. Here again, a number of substances available to those skilled in the art are listed in the introduction of this application. The options mentioned should not, however, be regarded as limiting the scope of the invention.

The sensors can be located in or on the substrate surface, i.e. they can be applied thereto as a thin pattern or buried in the substrate surface or arranged in some other way so that the substrate surface is planar. As the sensor patterns are usually extremely thin, particularly if sensors are provided for electrical detection, the terms "planar substrate surface" or "plane substrate surface" of course also encompass those substrate surfaces where the sensors lie on the substrate proper, e.g. a silicon wafer.

If the sensors are sensors for electrical detection, this being preferable, preferential use can be made of transducers, e.g. electrodes or field effect transistors. Instead, optical sensors or, where appropriate, chemical sensors can be employed. Preferably, the layer according to step (b) is applied in such a way and/or is patterned in such a way that the positions on the substrate surface where the sensors are located are not covered by the layer. This embodiment of the invention affords microcompartments and capturing-molecule-occupied arrays in which the sensors for optical or electrical detection are in direct contact or at least in very close proximity to the capturing molecules and consequently, during the measurement, to the analytes, or capturing molecule/analyte complexes, or capturing molecule/analyte combinations, to be detected.

The invention therefore provides detection systems comprising microcompartments or microcapillary reactors in which molecular immobilizations can be achieved on a mass production scale, but which are removed again from the substrate or sensor after molecules have been bound.

Furthermore, the invention provides specific detection systems which can be obtained with the aid of steps (a) to (d) of the above-specified method, while removal of the micropatterned layer according to step (e) can be dispensed with. These detection systems are characterized by specific geometries and possibly materials of the layer to be applied according to step (b).

Cost effective fabrication via semiconductor industry technologies and convenient handling are advantages of the invention.

Generating the separated microcompartments produced according to step (b) on e.g. silicon components is useful, for example, if a sensor array is to be coated with different molecules, e.g. DNA or RNA or their building blocks or proteins or peptides or other affinity-binding molecules, particularly in those cases where it is necessary for one liquid to be replaced by another. Conversely, such compartments are also required, however, in those cases where similar capturing molecules are bound in all the microcompartments and are then tested with different analytes which contain different substances or substance mixtures to be detected.

The planar substrate suitable for the invention can be made of customary materials, especially of silicon, glass or ceramics, the microcompartments generated allowing the use of wet-chemical methods for generating the molecular arrays without mutual contamination being the result. The invention accomplishes the microcompartments preferably with the aid of a layer of polymeric, or alternatively mineral or metallic materials. The designated array areas on the substrate or sensor elements in such a configuration are accessible via openings or channels to the liquids to be applied for the purpose of depositing the capturing molecules.

In a particular embodiment, disjunct regions or microcompartments are created in step (b), two microcompartments at a time being connected, however, by a channel to form a so-called microcapillary reactor. These microcapillary reactors are particularly suitable for complex reactions and for replacing one liquid by another, possibly by means of an additional stamp-like liquid distributor, inter alia with regard to deposition of the capturing molecules. After immobilization of identical or different molecules has been effected and after any washing processes, the side walls and top walls of these microcompartments or microcapillary reactors can be removed in accordance with step (e). This has the particular advantage that all the mechanical barriers for liquid exchange between the array positions are thus removed and purging, washing or detection processes important for utilization of the element are accelerated and enhanced.

According to the invention it is possible for materials prepatterned by stamping and/or photolithography to be applied to the substrate or the sensor element and to be fixed by gluing or hot-sealing or intrinsic adhesion. As an alternative, sheets or thin slabs can be applied as a whole. By means of conventional lithographic and/or etching techniques they are then opened up at the desired array positions and freed of the compartment-forming material.

The present invention is particularly suitable for sensor elements in which arrays of different molecules, molecular aggregates or entire biological cells must be locally deposited onto the various positions occupied by sensitive optical or electrical elements. One particular advantage of the invention is that the method can be readily combined with proven silicon technology and automated liquid distribution by means of dispenser or inkjet techniques. Elimination of the lateral border of the microcompartments after the molecular array has formed can be effected by mechanical removal or chemical stripping in such a gentle manner that sensitive biomolecular coatings are not affected. After the polymers have been removed, homogeneous wetting with liquids or other analytical media is possible without any troublesome surface patterns. The same techniques can also be used to immobilize identical types of molecules in a batch process in all the microcompartments or microcapillary reactors and then to load them for analytical studies with various analytes or reactants.

In a particular embodiment, permanent microcompartments having a low aspect ratio (height/diameter) are expounded, which have special protective contrivances against mixing.

DESCRIPTION OF THE FIGURES

FIG. 2 shows a plan view from above and sectional views of a planar arrays comprising microcapillary reactors and immobilized molecules at various stages of the fabrication process;

MEANING OF THE REFERENCE SYMBOLS

Figure 1:
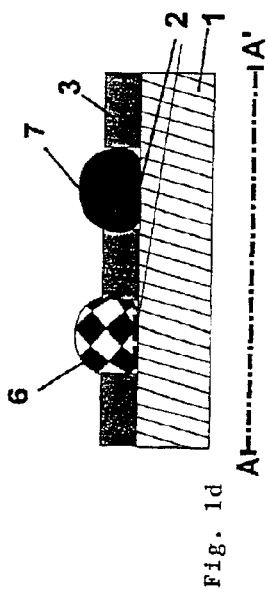
FIG. 1 shows a plan view from above and sectional views of a planar sensor array comprising microcompartments and immobilized molecules at various stages of the fabrication process.
Figure 1:
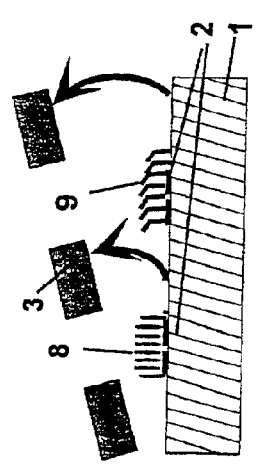
Figure 1:
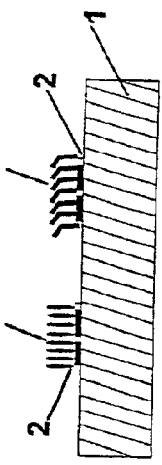
Figure 1:
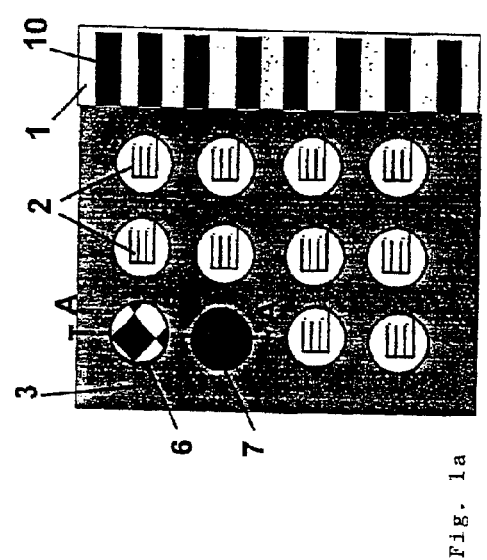
Figure 1:
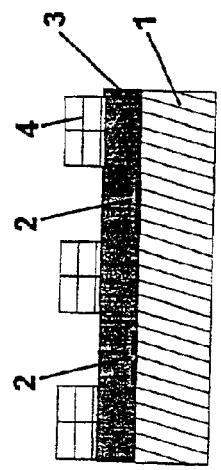
Figure 1:
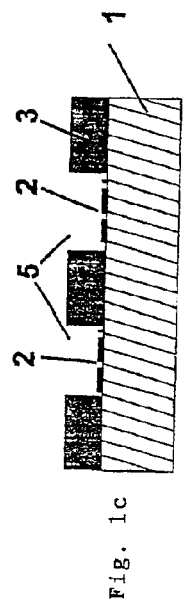

1 Substrate
2 Thin-film electrode
3 Polymer layer
4 Hole mask
5 Laterally delimited microcompartment
6 Droplet of liquid containing molecular type A
7 Droplet of liquid containing molecular type B
8 Immobilized molecular type A
9 Immobilized molecular type B
10 Chip contact
11 Capillary reactor inlet
12 Capillary reactor outlet
13 Capillary reactor channel
14 Photolithographic mask
15 Trench-like micropattern
16 Stamp inlet opening
17 Stamp outlet opening
18 Stamp inlet distribution channel
19 Stamp outlet distribution channel
20 Stamp made of polymer FIG. 1, by way of example, shows the fabrication and use of microcompartments via a patterned polymer coating on an electrode array in silicon technology. FIG. 1a shows the plan view from above of an array comprising 12 sensor electrodes 2 on an insulated silicon chip 1. The electrical chip contacts 10 serve as terminals by means of which electrical contact is made with the electrodes 2. In this arrangement, the conductor tracks run invisibly underneath the polymer film 3 and are separately covered by an insulator (not shown). The droplets of liquid 6 and 7 illustrate selective dosing into two of the laterally delimited microcompartments formed by the polymer 3. The sectional line A–A' in the figure marks the region shown in FIGS. 1b to 1f.

FIG. 1b shows a detail of the silicon substrate 1 along the sectional line A–A' with two electrodes 2 as sensor elements, which is covered by a polymer coating 3 applied on top of the entire element. Placed on top of this polymer is a hole mask 4.

FIG. 1c shows the arrangement as in FIG. 1b after removal of the polymer film 3 at the locations of the openings in the hole mask by means of dry-etching techniques, followed by conventional removal of the photolithographic mask 4. The microcompartments 5, thus formed with lateral walls, about the sensor electrodes 2 are shaped as cup-like depressions.

FIG. 1d shows the arrangement as in FIG. 1c after selective introduction or dosing of the droplets 6 and 7 contained dissolved chemical species A and B.

FIG. 1e shows the arrangement as in FIG. 1d after chemical binding of the molecules A8 and B9 when the polymer film 3 is stripped from the electrode array.

FIG. 1f shows the detail as in FIG. 1e after stripping of the polymer film 2 and represents the planar sensor array without mechanical barriers, which is employed for analytical application using immobilized molecular types A and B.

FIG. 2 shows the design and use of microcapillary reactors. To do this, according to FIG. 2a a prepatterned polymer layer 3 is attached to the silicon substrate 1 in section B–B' according to FIG. 2e. The microcapillary reactors prefabricated in the polymer by punching and embossing techniques consist of the inlet and outlet ports 11 and 12, which are connected to one another via a channel 13.

In FIG. 2b, the microcapillary reactor has been filled with a solution 7 through the inlet port 11, and the molecular type B8 is immobilized at the bottom of the microcapillary reactor.

FIG. 2c shows the mechanical removal of the polymer layer 3. As shown in FIG. 2d, this results in a planar molecular array as described above for FIG. 1f. In the process, the pattern of the microcapillary reactors is eliminated again.

FIG. 2e shows the plan view from above of an arrangement of microcapillary reactors on a chip substrate. Next to the inlet ports 11 and the outlet ports 12 in the polymer 3, the connecting channels 13, not visible from above, are indicated by black dashed lines. The dashed line B–B' shows the cross section detected in FIG. 2a. The sectional line B"–B"' shows a microcapillary reactor according to FIG. 2b, filled with liquid 7.

FIG. 3a shows a planar sensor array having a micropatterned surface. Depicted on the planar substrate 1 are nine microelectrode arrangements 2 in a polymer layer 3 comprising the sensor areas 5, the contacts 10 and a position filled with liquid at A–A' and trench-like depressions 15, which extend round the areas 5. The cross sections of FIGS. 3b, 3c and 3d correspond to the sectional line A–A' in FIG. 3a. FIGS. 3b and 3c show the fabrication of this pattern: the planar substrate 1 and the microelectrode arrangement 2, and the polymer layer 3 are covered in FIG. 3b by a photolithographic mask 14. In FIG. 3c, dry-etching has exposed the microelectrode arrangement 2 in the sensor area 5 and an micropattern comprising trench-like depressions 15. The sensor area 5 has in this representation already been filled with a droplet of liquid 7. FIG. 3d depicts a detail of a planar array comprising a micropattern of trench-like depressions 15 in the polymer layer 3 and the immobilized molecular type 8.

Figure 4:
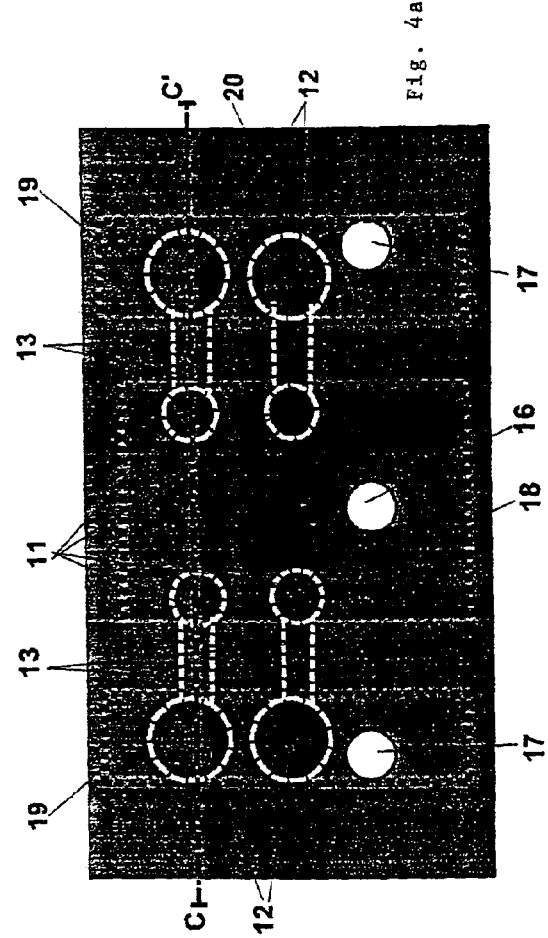
FIG. 4 shows a plan view from above and sectional views of a stamp for handling liquids on a planar array.
Figure 4:
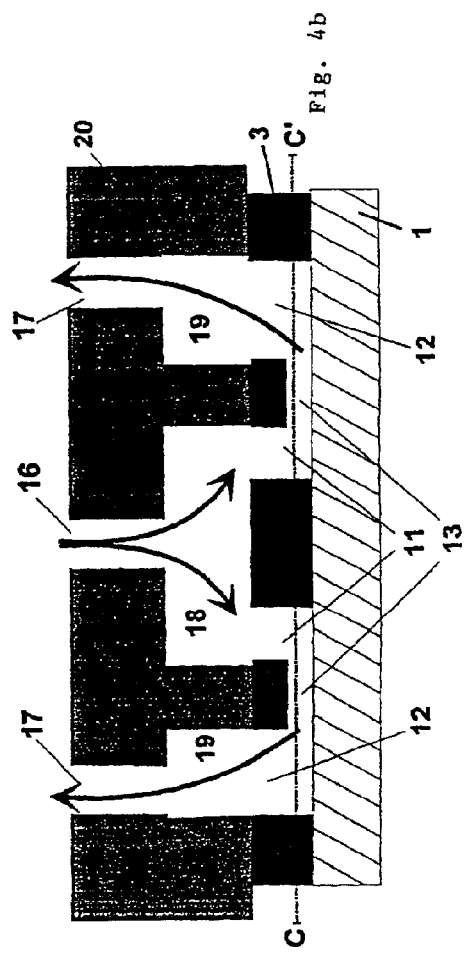

FIG. 4 shows the design of a stamp 20 for handling liquids on planar arrays 1 comprising microcapillary reactors (see also FIG. 2). FIG. 4a shows the plan view from above of a stamp by means of which the substrate can be covered, in its entirety or in part, with the microcapillary reactors as depicted in FIG. 2d. In the plan view from above FIG. 4a, an inlet opening 16 and two outlet openings 17 can be seen here. The black lines mark the cavities within the stamp, which, according to FIG. 4b, represent inlet distribution channels 18 and two outlet distribution channels 19. The white dashed lines indicate how the microcapillary reactors according to FIG. 2d are arranged underneath the stamp. In the cross section FIG. 4b, a stamp 20 has been set down on a sensor array 1 comprising the microcapillary reactors. The inlet opening 16 of the stamp is arranged above the inlet distribution channel 18 and the inlet ports 11 of the microcapillary reactors. Located above the outlet ports 12 of the microcapillary reactors are outlet distribution channels 19 which connect all the outlet ports 12 to the outlet openings 17 of the stamp. When liquids are applied, the microcompartments are filled through the inlet openings 16 of the stamp via the inlet distribution channel 16 and the inlet opening 16. Through the connection channels 13 of the microcapillary reactors, the liquid flows via the outlet ports 12 into the outlet distribution channels 19 of the stamp to the outlet opening 17 of the stamp, where the liquid can be drawn off again.

DETAILED DESCRIPTION OF THE INVENTION

An important principle of the invention is that various biomolecules such as peptides, proteins, oligonucleotides or nucleic acids are immobilized in a reliable and demarcated manner on defined, demarcated areas on a planar substrate, e.g. made of silicon, glass, ceramics or organic polymers or analogous or similar planar elements which are fitted with chemical, optical or electrical sensors. To do this, microcompartments laterally demarcated from one another are generated on the designated areas of the substrates or sensor elements, which microcompartments in a specific embodiment can be in the form of microcapillary reactors which can accommodate solutions e.g. containing different molecules, without these mixing. By means of customary chemical coupling reactions, e.g. using bifunctional reagents, molecules from such solutions are bound to the surface of the substrates or sensor elements, i.e. are immobilized, which subsequently can act as capturing molecules.

The microcompartments which can thus be fabricated (step (b) of the fabrication procedure) can have a circular, square or any other geometry. To produce them, polymeric materials, or alternatively mineral or metallic materials, can be used as the layer for the method according to the invention. Examples of potentially suitable polymers include polysiloxanes, polyamides, polymethacrylates, polycarbonates or polystyrenes. These are applied to the planar substrates or the planar sensor elements, which e.g. can be a complete silicon wafer or a glass sheet or alternatively an individual chip, and, if required, are affixed thereto. The adhesion of the materials for these microcompartments is achieved either via intrinsic adhesion or by hot-sealing techniques or by laser spot welding or by additional adhesives. At least in the region round the compartments, said adhesion should preferably effect a seal. Suitable tailoring of the properties of substrate and polymer and of the fastening method provides the option of later removal. To achieve this, polymers having suitable adhesion characteristics and having adequate resistance to the liquids used are selected, for example.

In an embodiment of the invention, polymer sheets, polymer films or thin polymer slabs are used for the layer which are first provided with predefined openings and are then affixed to the substrate or sensor element in such a way that the designated areas remain free from polymer and form a microcompartment. These areas are preferably those which carry sensors for subsequent detection of the analytes. The openings in question are preferably produced by punching processes or alternatively photolithographically or by means of hole masks, e.g. in combination with dry etching techniques. This affords the element shown in FIG. 1a in a process suitable for mass production.

This method has the advantage that sensitive surfaces in sensor elements such as optical gratings or alternatively electrodes are kept free of any contact with contaminants, contamination of the sensitive surfaces thus being avoided.

Microcompartments of step (b) can alternatively be produced by thin sheets of silicon, glass, metal or ceramics being cemented on. These materials are preferably patterned beforehand by means of standard microsystem technology processes and can be affixed to the substrates or sensor elements by means of peelable adhesives, as used, for example, with labels, or alternatively by hot-sealing polymers.

According to the invention, in an alternative embodiment of the method according to the invention, a polymer or its precursor can be used to generate the microcompartments according to step (b), said polymer being applied in liquid or paste-like form, or affixed in a self-supporting form as a whole (as a layer) in an unpatterned form to the substrate or a sensor element as described above. This polymer layer can be patterned photochemically according to known techniques, e.g. by exposing, by means of photoresist and conventional lithography or by hole masks, those desired areas, preferably above the sensor elements, which later are to represent the microcompartments. Subsequently, the material above the desired substrate surfaces and, if required, sensor elements is removed, e.g. by means of dry-etching techniques, to produce the laterally delimited microcompartments. This method is particularly suitable for producing microcompartment patterns in which trench-like depressions around the bioarrays proper are to remain, since these cannot be entirely achieved on a prefabricated (prepunched and/or preembossed) layer. Webs would have to remain here which hold up these patterns.

The result of both methods, either with prepatterned materials or with materials patterned on the substrates is that a substrate or a sensor element is then obtained which has microcompartments in the form of small cups or chambers, possibly surrounded by further depressions. As already mentioned, the geometric shape of these patterns is not subject to restrictions, so that the embodiments depicted in the figures with round openings of the areas, are only meant to represent examples. Neither the relative proportions of the ports and the tunnels of the microcapillary reactors are necessarily predefined, nor the geometric shape of the patterns. Those skilled in the art will define the most advantageous shape in each case on the basis of the envisaged fabrication methods, which can greatly differ from one another, given the wide variety of fabricating options. Other possibilities therefore include microcompartments which are angular (rectangular, square), oval or of some other shape.

The diameters or heights of the compartments are likewise not necessarily predefined. Advantageously, they can be in the range of between about $0.2 \mu m$ and several hundred $\mu m$. The ratio of diameter to height of the compartments can likewise be freely chosen, suitably e.g. being in the range of from 20:1 to 0.5:1, preferably from about 10:1 to 1:1.

The substrates or sensor elements fabricated in one of the abovementioned ways and comprising laterally delimited microcompartments (i.e. microcompartments which are mechanically demarcated from one another) can then, as shown in FIG. 1c or 2b, be filled with any solutions. In so doing, the volume to be chosen of the microcompartments generated is tailored to the dosing means such as micropipettes, inkjet technology or other dosing techniques and to the chemical reactions envisaged or the given sensor functions. The liquid volumes preferably vary between about 5–500 pl, in the case of piezo-dosing and about 1 nl to a few $\mu l$ in the case of pipeting devices. The dosing liquids can be used both to apply into the various microcompartments both the reagents for immobilizing the capturing molecules and various biomolecules (which e.g. are intended as capturing molecules).

For this purpose, the designated surfaces, particularly if they are substrate surfaces, are reacted with short-chain, reactive, bifunctional molecules in solution or from the gas phase. Examples of these molecules in principle are any molecules which react with a substrate, in the case of inorganic substrates (silicon, $SiO_2$, $SiON_x$, types of glass) therefore molecules which carry groups such as e.g. chloral alkyl- or chloral aryl silanes, chloral aromatic compounds, alkox alkyl-/alkox aryl silanes or mixtures from these components and which have a second reactive group, such as e.g. aldehyde, isocyanate, cyanate, thiocyanate, thiol derivative or thio ester at the other end of the molecule, which preferably has the form of a spacer molecule. To couple any organic molecules required, particular biomolecules such as RNA and DNA molecules, proteins, peptides and oligonucleotides, to these, equivalent principal methods are used as described for coupling with hydrophobic molecular radicals. Options here include both direct coupling and spacer coupling via the abovementioned silane and halogen groups to the substrate or sensor surfaces.

A possible alternative immobilization variant is self-assembling monolayer formation. This is suitable especially in those cases where the surfaces of metallic sensors (e.g. of transducers such as electrodes or the like) are to be loaded with a capturing molecule. For example, thiol derivatives, e.g. 1-thiol-n-amino alkanes, can be applied to gold surfaces of sensors or adjacent auxiliary faces close to sensors (transducers or the like). A special feature when coupling biomolecules onto the above-described array patterns is the option of simultaneously activating all cavities in a batch process in such a way that subsequently different types of molecules are introduced into the individual compartments and are immobilized as described above.

This can be achieved, as shown in FIG. 1e, by selecting microcompartments or microcapillary reactors and carrying out different chemical reactions in these. After the chemical reactions have been carried out, e.g. after immobilization of a so-called molecular library, the polymer 3 can again be removed from the substrate or the sensor element. This can for example be achieved mechanically, like a peeling process, optionally thermally aided. Suitable polymers can also be removed by stripping with solvents against which the immobilized molecules are resistant. For example, polymethacrylates, polycarbonates can inter alia be removed with the aid of solvents such as acetone or methyl acetate, whereas an oligonucleotide library is not effected by this and remains bound. If sensitive types of molecules such as proteins, especially enzymes, antibodies and the like, are immobilized, the reagent-free mechanical removal of the microcompartments without causing any thermal stress is particularly advantageous.

The substrates or sensor elements, having been covered with various molecular species and having been freed of the compartments, have an essentially ideally planar surface which permits the unhindered replacement of liquids, washing processes or homogeneous analytical operations, permitting both the measurement of one analyte in a multiplicity of samples to be applied or the measurement of a multiplicity of possible analytes (e.g. with the aid of a library of oligonucleotides which was arranged on the array positions) in a single sample.

In a special performance variant, the polymer material for the layer to be used in step (b) of the method according to the invention is Teflon which is spun on as a film like a photoresist onto e.g. a silicon wafer and is affixed to the wafer according to standard methods, making use of adhesion promoters. As described above, hole masks or photolithography is then used to remove the Teflon material from the designated positions, resulting in microcompartments corresponding to FIG. 1. The height of these microcompartments in this embodiment variant can be reduced to only from 0.5 to about 10 $\mu$m. If a ratio of the diameter of the compartments to the height of the polymer layer of about 10:1 or greater is chosen, the Teflon polymers can remain on the wafer without representing a substantial mechanical obstacle to rinsing processes or analyte access. The advantage of using this Teflon resides in its markedly hydrophobic behavior. In such an arrangement, even the low heights of the rims of the microcompartments together with the hydrophobic, i.e. water-repellent coatings of the interstices are very effective as barrier elements between the individual compartments, so that the remaining patterns of the layer, given their low heights, do not have any drawbacks compared with the detection system in which this layer has been completely removed. In embodiments employing a markedly hydrophobic layer, detection systems are therefore suitable even if step (e) of the method according to the invention (stripping of the micropatterned layer) is dispensed with, as long as such a height of the patterned layer is chosen as not to impede rinsing processes and the like.

Alternatively, a Teflon layer can also be applied in self-supporting form to the substrate, said layer optionally being capable of being pattered prior to application (e.g. by punching) or afterwards.

In another embodiment of the invention, particularly for very small compartment volumes or if poorly wetting liquids are dosed, the microcompartments are fabricated, as already mentioned, in the form of so-called microcapillary reactors. These capillary reactors, as shown in FIG. 2a, consist of two microcompartments 11 and 12, in a similar arrangement as described above for FIG. 1, which are connected to one another via a capillary-like channel 13.

In this embodiment of the invention, the ports and the channels are preferably prefabricated by punching and embossing from (organo)polymeric, mineral or metallic material or, where appropriate, by a combination of lithography and etching processes and are affixed to the substrate or sensor element as described in the above case of the individual compartments. Alternatively, only the channels are prefabricated, e.g. by embossing or etching, and the inlet and outlet ports are generated as described above for the microcompartments, e.g. not until after application to the substrate surface.

The arrangement of a microcapillary reactor acts like a system of communicating whistles. Because of the small sizes of compartment and channel in dimensions of from 1 $\mu$m to about 1 mm, preferably 50–500 $\mu$m, capillary forces are active during the liquid-filling operation.

If a liquid is applied into one of the compartments, which can just as well be the same size or smaller or larger than the other, the effect of the capillary forces is that the second compartment fills spontaneously via the channel without additional expedience. A further advantage is that the applied liquid displaces any gas present in the microcompartments and the channel through the second port and thus reliably prevents gas bubbles from remaining behind. It is therefore even possible to dose these microcapillary reactors with droplets which are larger than the port of one of the compartments, as the capillary forces cause such a droplet to be drawn in spontaneously. The arrangement of the capillary reactor moreover also permits direct filling from a capillary placed onto one of the compartment ports. After such a liquid-filled capillary has made contact, the system spontaneously draws in the liquid until it is full, without any spillage being observed. Apart from the particularly simple pipetting methods, piezo or other inkjet dosing techniques can be used for filling. The system of the capillary rector can also be used to feed in identical liquids or for efficiently replacing one liquid by another, as often required in chemical reactions or immobilization methods. In the simplest case, such a washing operation is achieved by placing one capillary for dosing purposes at or onto a compartment port and drawing off with suction from the second compartment port by means of a second capillary.

The detection system in this embodiment of the invention can either, according to step (e) of the fabrication method according to the invention, be freed of the micropatterned layer after the capturing molecules have been applied to the surface of the substrate. In a special embodiment, however, the microcapillary reactors can remain on the substrate even during detection of the analytes. This is advantageous, for example, in those cases where the capillary action of the microreactors can also be beneficially utilized for steps during the detection, e.g. when a multiplicity of analyte liquids is applied with the aid of dosing techniques such as stamping or inkjet techniques, or if the quantity of the analyte liquid to be measured in the microcompartment is required to be controllable with some accuracy.

In a further embodiment, photopatternable polyimide (or some other suitable, preferably hydrophobic organic polymer material) is used, according to standard procedures, as a material for microcompartments and additional trench-like patterns. As described above, microcompartments preferably having a height of about 50–200 µm are produced photolithographically or by dry etching. Additionally, in this embodiment, the sensor areas are surrounded by annular, trench-like patterns, e.g. dimensions with a width of between 10 and 100 µm (see FIG. 3). Optionally, a few relatively wide or alternatively many correspondingly narrow patterns can be arranged. The effect of the hydrophobic character of the polyimide, similar to what was expounded for the coating with Teflon, is to cause aqueous solutions to be repelled. When droplets are dosed into the sensor areas, the risk of spill-over into an adjacent cavity is decisively reduced by the trench-like patterns which are able to accommodate liquid material. Compared with an areal interstice between the compartments, three separating effects are active here: firstly, the hydrophobicity of the polyimide, secondly the volume of the trench-like patterns which are able to accommodate liquid, and thirdly the edge characteristics of the micropatterns, which prevent droplets from flowing off in the way the edge of a plane surface would. As the dynamic contact angles of hydrophilic liquids and hydrophobic substrates are known or can be measured, the volume of the applied liquid droplets can be calculated with relative accuracy in such embodiments, thereby allowing quantitatively definable amounts of capturing molecules to be applied to the substrate. For this reason, for example, it may be advantageous in this embodiment of the invention not to free the detection system from the micropatterned layer according to step (e) of the method according to the invention, but to detect the analyte(s) in the demarcated microcompartments laterally surrounded by the trench-like patterns. This should not be the rule, however, particularly if patterns present on the substrate impede necessary washing processes or the like which have to be carried out over the entire chip or wafer.

Both to dose the solutions used and to remove then with suction, capillaries are drawn out in such a way that the outside diameter at their tip match the micropattern on the detection system, e.g. is about 2–10 µm. The capillary tips are consequently relatively small, in proportion to the individual array positions. The volumes separately dispensable owing to these capillaries are in the lower nl range, and consequently likewise very small in relation to the total volume in a microcompartment or in a microcapillary reactor, being about 5–10% of this total volume. Alternatively, piezo dozing heads are used to introduce pl amounts of the solutions in question into microcompartments or into a microcapillary reactor in a contact-free manner. Here, the dimension of the incident pl droplet jet is even smaller in relation to the dimension of the array position.

To use the glass capillaries for dosing various solvents, the polarity of the outside of the glass capillary can be adjusted by chemical modification counter to the polarity of the solution used in each particular case. For example, after the outside of the capillary has been hydrophobized with chlorosilane, aqueous solutions can be dosed in a defined and loss-free manner, since retrograde migration of droplets escaped from the capillary tip no longer occurs. The converse solution is employed for dosing organic solvents. Given a hydrophilic outside of the capillary tip, retrograde migration of the escaped droplets is no longer possible.

In the case of planar patterns and microcompartments, evaporation of aqueous solutions can be effectively prevented by storing under saturated water vapor atmosphere. Additionally, there is the option of preventing losses in volume due to evaporation by means of sheets laid on or glued on. Without this measure the liquid applied will dry off within 0.5 min in the case of planar patterns and within a few minutes in the case of microcompartments.

Figure 3:
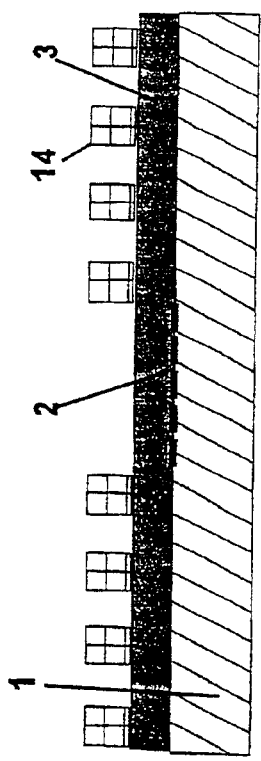
FIG. 3 shows a plan view from above and sectional views of a planar sensor array comprising patterned surfaces and immobilized molecules.
Figure 3:
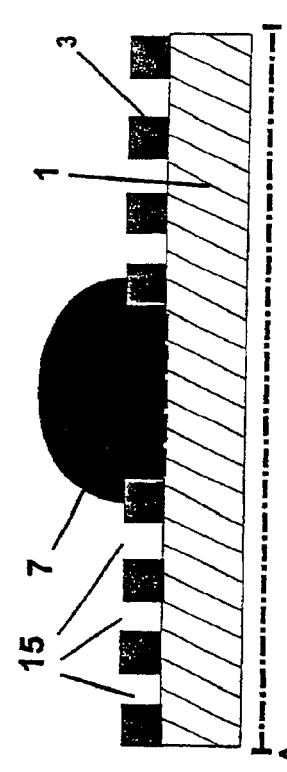
Figure 3:
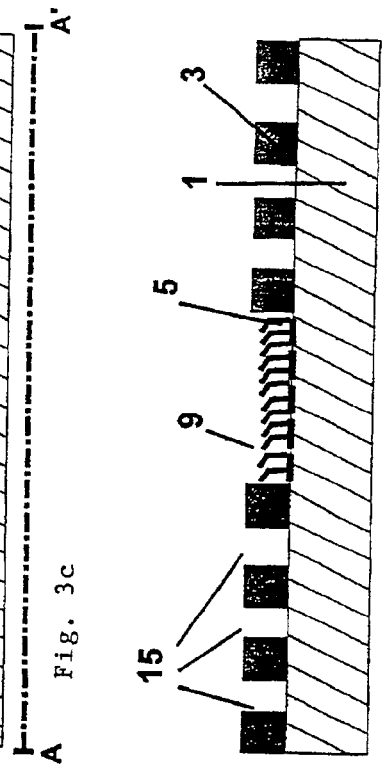
Figure 3:
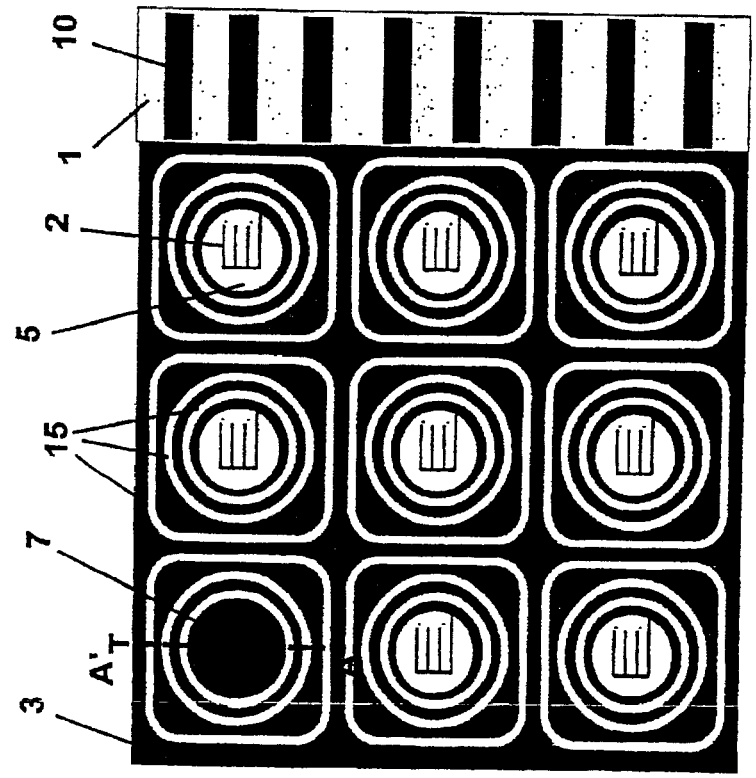

Filling and removal with suction can equally be effected by setting down a stamp 20 which is complementary to the pattern shown in FIG. 3. Via the stamp, a plurality or all of the inlet ports 11 of the microcapillary reactors are connected to one another via a distribution channel 18 in the stamp 20, as shown in FIG. 4. In the same way, the various outflow ports 12 of the capillary reactors in the array are connected to one another by the distribution channels 19. This can be implemented row by row or over the entire array, so that inlet and outlet openings 16 and 17, respectively, can be used to pressure-flush or pressure-charge the entire microcapillary reactor array. To do this, liquid is supplied via hoses from suitable reservoirs or filling devices to the inlet opening 16 and is discharged again via the second channel system through the outlet opening 17 in the stamp. Such stamps can preferably be fabricated from sealing polymers or rubber-like materials such as silicones, polyamides or polyhydrocarbons. Metal or silicon stamps with thin resilient seals are also suitable, however. In the case of glass or silicon materials, the conventional etching techniques for producing micropatterns can be employed to particular advantage.

After reactions in the arrays and/or immobilization of molecules on the bottom faces of the compartments located on the substrates or sensor elements, the material layer forming the microcapillary reactor can be removed, in the same way as described for the "simple" microcompartment arrays. According to the invention, this affords a planar molecular array without mechanical obstacles between individual positions.

The invention will be described below in more detail with reference to exemplary embodiments.

EXAMPLE 1

Fabrication of an Electric Sensor Array

Microelectrode patterns according to FIG. 1 are fabricated in standard silicon technology. [K. Reimer et al. Sensors and Actuators, A 46/47 (1995) 66]. To do this, 500 nm thick thermal oxide is generated on 4" silicon wafers. On the oxide, resist is patterned photolithographically in such a way that the contours of the electrodes for the electrode patterns are exposed. The electrode system according to details in FIG. 1a consists of comb-like electrode strips of a width of 1.5 µm with a spacing of 800 nm. The electrode strips are connected to the pads 10 via conductor tracks (not visible) underneath the insulation 3. Twelve sensor array positions are arranged on the sensor array in a 4×4 matrix comprising array positions having a diameter of 300 µm. The spacings of the sensor array positions are 400 µm, resulting in an active sensor array region of about 2.5 mm×2.5 mm.

Using a photolithographic mask, the patterns of the electrodes are imparted to the silicon dioxide-coated wafer. A titanium bonding layer having a thickness of 20 nm and a gold layer having a thickness of 150 nm are vapor-deposited over the entire surface by means of an electron beam. Via a lift-off process, all the material between the electrodes, conductor tracks and contacts is removed. The wafer is then covered with a silicon oxynitride layer having a thickness of 400 nm, which is generated in a plasma by chemical deposition (PECVD-SiN$_x$:H). Subsequently, the array positions and the pads situated on the outside are exposed down to the gold surfaces by reactive chemical dry etching. After a protective coating has been spun on, the wafer is sawn from the rear to a depth of about 250 µm according to the designated individual chip edges.

EXAMPLE 2
Formation of Microcompartments Using Prefabricated Polymers by Hot-sealing Electric sensor arrays fabricated according to Example 1 are freed from protective coating in an ultrasonic bath with acetone and are washed repeatedly with alcohol and ultrapure water. In the next step, while still joined together as a wafer, they are loaded with microcompartments by a preperforated polypropylene sheet having a thickness of 400 µm being laminated on. The perforation corresponds to the sizes of the sensor array positions and the pads. The lamination is effected by means of heating via a stamp. Strips about 200 µm wide are sealed around the array positions. The alignment of the sheet applied in wafer size by means of a vacuum stamp is carried out by optical checks by means of fiducial marks on the wafer surface. The wafer cooled to −20° C. is broken along the chip edges presawn according to Example 1, thus affording the individual chips.

EXAMPLE 3
Formation of Microcompartments Using Prefabricated Polymers by Laminating Optical sensor arrays consisting of glass wafers which are homogeneously provided with a light-conducting layer of silicon oxynitride and a silicon dioxide layer of about 20 nm are sawn from the rear in accordance with Example 1. Then they are freed from protective coating in an ultrasonic bath with acetone and are washed repeatedly with alcohol and ultrapure water.

In the next step, a 0.3 mm polypropylene sheet is affixed over the entire surface by means of an adhesive which can be removed without residues. After a hole mask of etched silicon having a thickness of 0.6 mm has been put on top of this, a hole arrangement corresponding to the desired array positions and microcompartments is employed to etch away the polymeric material in accordance with the array positions down to the silicon dioxide layer by means of the active dry etching. Reactive plasma is used for this. The wafer cooled to −20° C. is broken along the chip edges presawn according to Example 1, thus affording the individual chips.

EXAMPLE 4
Formation of Microcapillary Reactors

Electric sensor arrays fabricated according to Example 1 are freed from protective coating in an ultrasonic bath with acetone and are washed repeatedly with alcohol and ultrapure water. In the next step, they are provided with a preperforated polyamide disk having a thickness of 0.5 mm in wafer format by gluing similarly to Example 3. To produce the microcapillary reactors, the connection channels having a length of 100 µm are embossed beforehand into the polymer disk. The inlet and outlet ports are fabricated like the microcompartments in Example 3. The inlet ports have a diameter of 200 µm and the outlet ports a diameter of 300 µm. The wafer cooled to −20° C. is broken along the chip edges presawn according to Example 1, thus affording the individual chips.

EXAMPLE 5
Formation of Microcompartments by Means of Photolithographically Patterned Polymers Electric sensor arrays still joined together as a wafer according to Example 1 are freed from protective coating in an ultrasonic bath with acetone and are washed repeatedly with alcohol and ultrapure water. Then they are coated with a film having a thickness of 15 µm, using Teflon AF (DuPont) in a spin-coating process. Beforehand, the entire wafer is wetted with the appropriate adhesion promoter (DuPont). After baking of the Teflon layer at 150° C. for 20 min, a photolithographic mask having the patterns of the array positions and the trench-like depressions according to 15 in FIG. 3a and the pads is applied. By means of reactive dry etching, the Teflon is exposed from the areas of the array positions and the pads and from the trench-like patterns down to the surfaces of the electrodes or the substrate surface.

As an alternative to Teflon AF, the polymer layer can also be prepared from standard polyimide and patterned in an identical manner. The wafer is broken along the chip edges presawn according to Example 1, thus affording the individual chips.

EXAMPLE 6
Immobilization of Oligonucleotides on Sensor Arrays

A chip fabricated according to Example 3 is mounted on a ceramic support carrying standard collector tracks and is wire-bonded. As a result of a polymeric molding of polysiloxane being glued on along the chip edges to circumscribe the active electrode areas, a reaction vessel having a diameter of about 5 mm is affixed to the chip. This reaction vessel is filled with a 5 mM solution of 11-mercapto undecanylamine in cyclohexanone, which is covered and left at room temperature for 5 hours. Loading of the electrodes by self-assembling is monitored by an online impedance measurement (EG&G Model 398).

Said loading of the metal surfaces can alternatively also be achieved prior to breaking and separating the chips by the entire wafer, from which the coating has first been stripped, being dipped into the analogous solutions.

The chip surface now derivatized with amino functions is then incubated with a droplet (0.1–10 µl) of 20 mM of tolylene-2,4 diisocyanate (TDI) in ethyl acetate (EA) at room temperature for 10–60 min. It is washed with EA and dried.

After a chip thus activated has been washed with neutral phosphate buffer solution, 5 nl each of 24mer-oligonucleotide carrying an iodoacetyl group at the 5' terminus are successively introduced into each sensor array position by means of microcapillary dosing.

The nucleotide sequence is different at each array position, corresponding to the different target DNA molecules to be analyzed. The reactive liquids correspond to the volumes of the microcompartments. The coupling reaction proceeds spontaneously for one hour at room temperature. After covalent binding has occurred, the electric sensor array is washed with SSPE buffer (0.9 M NaCl, 50 mM NaH$_2$PO$_4$, 5 mM Na$_2$EDTA, pH 7.5).

The abovementioned patterned polymer coatings are removed from the chips by mechanical peeling.

EXAMPLE 7
Immobilization of Antigen Proteins on Sensor Arrays

A chip fabricated according to Example 5 is mounted on a ceramic support carrying standard collector tracks and is wire-bonded.

As a result of a polymeric molding of polysiloxane being glued on along the chip edges and circumscribing the active electrode areas, a reaction vessel having a diameter of about 5 mm is affixed to the chip. The surfaces situated within this ring are washed with alcohol and distilled water.

Immediately afterwards, the surfaces are silanized in the array positions by incubation in toluene with the addition of a silane (e.g. aminopropyltriethoxysilane; isocyanatopropyltriethoxysilane; glycidoxypropyltrimethoxysilane) ad 1–5% (v/v) at 40–80° C. for 1–30 h. Repeated washing in toluene is followed by tempering for 0.5–2 h in a drying oven at 60–80° C. The surfaces thus derivatized with secondary chemical functions are then directly incubated at room temperature for 10–60 min with a droplet (0.1–10 $\mu$l) of 20 mM of tolylene-2,4 diisocyanate (TDI) in ethyl acetate (EA). After washing with EA followed by drying, a droplet (0.1–10 $\mu$l) of another antigen protein solution ($C_{protein}$ about 1–10 mg/ml in carbonate buffer or phosphate buffer pH 9.5) was applied to each microcompartment and incubated at room temperature for 0.1–2 h.

The abovementioned patterned polymer coatings are removed from the chips by mechanical peeling.

EXAMPLE 8
Employing a Stamp for Affinity-Bonding of DNA on Sensor Arrays

Electric sensor arrays are fabricated according to Example 1, the actuators being in the form of interdigital electrodes (M. Paeschke et al., Analytica Chimica Acta 305 (1995) 126]. According to Example 4, they are provided with microcapillary reactors and according to Example 6 they are loaded with various oligonucletides.

A stamp corresponding to FIG. 4 is affixed to the array under mechanical pressure. DNA analyte as a mixture is then fed into the microcapillary reactors via the stamp inlet 16. Use is made of analyte DNA into which biotinylated primer biotin residues were introduced during conventional amplification of the DNA by means of PCR. The analyte DNA in SSPE buffer is converted to a concentration of 1 $\mu$g/ml, using Denhardt's solution (0.5 g of Ficoll, 0.5 g of poly (vinylpyrrolidone), 0.5 g of RSA in 0.5 l of $H_2O$) and applied to the sensor array and incubated for 2 h at room temperature. To remove excess analyte DNA, a washing step is carried out at 40° C. with SSC buffer (52.6 g of NaCl, 26.5 g of Na citrate in 0.8 l of $H_2O$) by flushing the flushing liquid under pressure through stamp and reactors and drawing it off at the outlet openings 17.

The detection of bound DNA is carried out after labeling with streptavidin/alkaline phosphatase conjugates and renewed washing, by electrochemical redox recycling [Hintsche et al. in Frontiers in Biosensorics/Fundamental Aspects, eds. F. W. Scheller et al., Birkhäuser Verlag Basel, Switzerland 1997, p 2781]in each array position.

The invention is therefore inter alia directed at a method for fabricating a molecular array on which molecules are immobilized on planar substrates or sensor elements by means of microcompartments or microcapillary reactors, with molecular arrays having planar surfaces being produced. The method can be used to produce temporary microcompartments in additionally applied layers and openings with access to the surface on planar substrates or sensor elements. These temporary microcompartments can be produced by additionally applied perforated layers with openings and access to the surface on the planar substrates or sensor elements. In the process, two microcompartments each can be connected together by a channel to form a microcapillary reactor whose bottom is formed by the surface of the planar substrates or sensor elements. The microcompartments or the microcapillary reactors can consist of (different, but optionally also identical) polymeric or metallic or mineral materials, as can the planar substrates or sensor elements. The sensor elements can be multiply disposed optical or electric transducers. To form the microcompartments or microcapillary reactors, the materials are preferably releasably bonded to the substrate. They can be preperforated or prestamped (e.g. in the form of (self-supporting) layers), resulting in patterns which correspond to the microcompartments or microcapillary reactors, or they can be transformed into these from prefabricated subpatterns by additional steps. The microcapillary reactors and/or microcompartments can be produced by photolithographic processes in combination with wet-etching techniques or reactive dry etching at the desired locations by creating the appropriate volumes of the microcompartments or microcapillary reactors. Their surface formed by the substrate or sensor elements should be freely accessible to chemical reactors, thus allowing capturing molecules to be arranged thereon. The materials of the microcompartments can then be removed again by physical or chemical means. A stamp matching the measurements of the microcapillary reactors and equipped with fluidic channels can be set down on these, allowing the reactors to be provided with liquid in pairs, in rows or in toto.

The arrays which can be fabricated according to the invention can be used for affinity binding of DNA.

What is claimed is:

1. Method of fabricating a detection system for detecting various analytes in one sample or for detecting one analyte in a multiplicity of samples, comprising a planar or essentially planar substrate surface and, arranged on said surface, arrays of analyte-binding capturing molecules, characterized by the following steps:

(a) providing a planar or essentially planar substrate with more than one sensor for the chemical, optical or electrical detection of the analytes which are arranged directly on or in the surface of the substrate, (b) applying a layer to the substrate, said layer being either already micropatterned or applying a continuous layer to the substrate and micropatterning the layer, in each case in such a way that disjunct regions of the substrate, on or in whose surface sensors are arranged, are not covered by the layer, where layer and substrate are sealingly joined to one another at least around the uncovered regions, (c) bringing at least part of the uncovered regions into contact with at least one liquid which contains capturing molecules, in such a way that the capturing molecules are capable of adhering to the substrate surface and/or to the surface of the sensors or to bind thereto, (d) removing the non-adhering constituents of the liquid, (e) removing the micropatterned layer or parts of said layer.

2. Method according to claim 1, characterized in that in step (b) the disjunct regions of the substrate, which are not covered by the layer, are given the form of microcapillary reactors which are formed by two openings in the layer and a connection between these openings, said connection being in contact with the substrate surface.

3. Method according to claim 1, characterized in that step (b) results in a structure wherein the individual disjunct regions of the substrate which are not covered by the layer are surrounded by one or more webs whose width is from 1/20 to 1/1 of a diameter of the disjunct, bare regions, said web or webs each being surrounded by a trench-like depression which extend or extends around the web and has or have a width in a range of from 1/20 to 1/1 of the diameter of said bare regions.

4. Method according to claim 1, characterized in that in step (b) an organic or partially organic polymer or its precursors is applied to the substrate and is patterned by means of lithographic methods and/or etching methods.

5. Method according to claim 1, characterized in that in step (b) a layer of self-supporting polymer, is attached to the substrate, said layer either having been previously micropatterned or being micropatterned on the substrate.

6. Method according to claim 5, characterized in that said attaching is effected with an aid of a subsequently strippable adhesive or by hot-sealing with polymers or by laser welding.

7. Method according to claim 5, characterized in that the layer of the self-supporting polymer comprises a polymer sheet, a polymer film or a thin polymer slab.

8. Method according to claim 1, characterized in that in step (b) a layer of an inorganic material which had previously been micropatterned is attached to the substrate.

9. Method according to claim 8, characterized in that said attaching is effected with an aid of a subsequently strippable adhesive or by hot-sealing with polymers or by laser welding, and that said layer of inorganic material comprises a silicon, glass, metal or ceramic plate, which had previously been micropatterned by stamping or by photolithography.

10. Method according to claim 1, characterized in that the layer before being affixed to the substrate was additionally provided with embossings.

11. Method according to claim 1, characterized in that a patterned layer in step (e) is stripped off mechanically or chemically.

12. Method according to claim 1, characterized in that step (b) results in a structure wherein the individual disjunct regions of the substrate which are not covered by the layer are surrounded by one or more webs whose width is from 1/10 to 1/3 of a diameter of the disjunct, bare regions, said web or webs each being surrounded by a trench-like depression which extend or extends around the web and has or have a width in a range of 1/10 to 1/3 of the diameter of said bare regions.

13. Method of claim 1, wherein the sensors comprise optical detection sensors.

14. Method of claim 1, wherein the sensors comprise electrical detection sensors.

15. Method of claim 1, wherein the sensors comprise chemical detection sensors.

16. Detection system for detecting various analytes in one sample or for detecting one analyte in a multiplicity of samples, comprising a planar or essentially planar substrate surface and, arranged on said plane, arrays which are provided for analyte-binding capturing molecules, comprising the following components:

(a) planar substrate with sensors for the chemical, optical or electrical detection which are arranged directly on or in the surface of the substrate, (b) a layer which is disposed on said substrate and is micropatterned in such a way that disjunct regions of the substrate, on or in whose surface the sensors are arranged, are not covered by the layer, where layer and substrate are sealingly joined to one another at least around the uncovered regions, characterized in that either (i) the layer applied to the substrate consists of a hydrophobic material and has a thickness of not more than 20 μm, or (ii) the disjunct regions of the substrate, which are not covered by the layer, are in the form of microcapillary reactors which are formed by two openings in the layer and a connection between these openings, said connection being in contact with the substrate surface, or (iii) the individual disjunct regions of the substrate which are not covered by the layer are surrounded by one or more webs, said web or webs each being surrounded by a trench-like depression which extend or extends around the web.

17. System according to claim 16, characterized in that the layer applied to the substrate consists of a hydrophobic material and has a thickness of not more than 20 μm.

18. System according to claim 17, characterized in that the layer applied to the substrate consists of a hydrophobic material and has a thickness of not more than 10 μm.

19. System according to claim 17, characterized in that the layer applied to the substrate consists of a hydrophobic material and has a thickness of not more than 1 μm.

20. System according to claim 16, characterized in that the disjunct regions of the substrate, which are not covered by the layer, are in the form of microcapillary reactors which are formed by two openings in the layer and a connection between these openings, said connection being in contact with the substrate surface.

21. System according to claim 16, characterized in that the individual disjunct regions of the substrate which are not covered by the layer are surrounded by one or more webs, said web or webs each being surrounded by a trench-like depression which extends or extend around the web.

22. System according to claim 21, characterized in that the individual disjunct regions of the substrate which are not covered by the layer are surrounded by one or more webs whose width is from 1/20 to 1/1 of a diameter of the disjunct, bare regions, said web or webs each being surrounded by a trench-like depression which extend or extends around the web and has or have a width in a range of from 1/20 to 1/1 of the diameter of said bare regions.

23. System according to claim 21, characterized in that the individual disjunct regions of the substrate which are not covered by the layer are surrounded by one or more webs whose width is from 1/10 to 1/3 of a diameter of the disjunct, bare regions, said web or webs each being surrounded by a trench-like depression which extend or extends around the web and has or have a width in a range of from 1/10 to 1/3 of the diameter of said bare regions.

24. System according to claim 16, wherein:
the layer applied to the substrate consists of a hydrophobic material and has a thickness of not more than 20 μm; and
the disjunct regions of the substrate, which are not covered by the layer, are in the form of microcapillary reactors which are formed by two openings in the layer and a connection between these openings, said connection being in contact with the substrate surface.

25. System according to claim 16, wherein:
the layer applied to the substrate consists of a hydrophobic material and has a thickness of not more than 20 μm; and
the individual disjunct regions of the substrate which are not covered by the layer are surrounded by one or more webs, said web or webs each being surrounded by a trench-like depression which extends or extend around the web.

26. System of claim 16, wherein the sensors comprise optical detection sensors.

27. System of claim 16, wherein the sensors comprise electrical detection sensors.

28. System of claim 16, wherein the sensors comprise chemical detection sensor.

29. Detection system for detecting various analytes in one sample or for detecting one analyte in a multiplicity of samples, comprising a planar or essentially planar substrate surface and, arranged on said plane, arrays of analyte-binding capturing molecules, comprising the following components:

(a) planar substrate with sensors for the chemical, optical or electrical detection, which are arranged directly on or in the surface of the substrate, (b) a layer which is disposed on said substrate, on or in whose surface the sensors are disposed, and which is micropatterned in such a way that disjunct regions of the substrate are not covered by the layer, where layer and substrate are sealingly joined to one another at least around the uncovered regions, (c) analyte-binding capturing molecules which are located on the surface of regions of the substrate which are not covered by the layer, and/or on the surface of sensors, characterized in that either (i) the layer applied to the substrate consists of a hydrophobic material and has a thickness of not more than 20 $\mu$m, or (ii) the disjunct regions of the substrate, which are not covered by the layer, are in the form of microcapillary reactors which are formed by two openings in the layer and a connection between these openings, said connection being in contact with the substrate surface, or (iii) the individual disjunct regions of the substrate which are not covered by the layer are surrounded by one or more webs, said web or webs each being surrounded by a trench-like depression which extend or extends around the web.

30. System according to claim 29, characterized in that the layer applied to the substrate consists of a hydrophobic material and has a thickness of not more than 20 $\mu$m.

31. System according to claim 30, characterized in that the layer applied to the substrate consists of a hydrophobic material and has a thickness of not more than 10 $\mu$m.

32. System according to claim 30, characterized in that the layer applied to the substrate consists of a hydrophobic material and has a thickness of not more than 1 $\mu$m.

33. System according to claim 29, characterized in that the disjunct regions of the substrate, which are not covered by the layer, are in the form of microcapillary reactors which are formed by two openings in the layer and a connection between these openings, said connection being in contact with the substrate surface.

34. System according to claim 29, characterized in that the individual disjunct regions of the substrate which are not covered by the layer are surrounded by one or more webs, said web or webs each being surrounded by a trench-like depression which extends or extend around the web.

35. System according to claim 34, characterized in that the individual disjunct regions of the substrate which are not covered by the layer are surrounded by one or more webs whose width is from 1/20 to 1/1 of a diameter of the disjunct, bare regions, said web or webs each being surrounded by a trench-like depression which extend or extends around the web and has or have a width in a range of from 1/20 to 1/1 of the diameter of said bare regions.

36. System according to claim 34, characterized in that the individual disjunct regions of the substrate which are not covered by the layer are surrounded by one or more webs whose width is from 1/10 to 1/3 of a diameter of the disjunct, bare regions, said web or webs each being surrounded by a trench-like depression which extend or extends around the web and has or have a width in a range of from 1/10 to 1/3 of the diameter of said bare regions.

37. System according to claim 29, wherein:

the layer applied to the substrate consists of a hydrophobic material and has a thickness of not more than 20 $\mu$m; and the disjunct regions of the substrate, which are not covered by the layer, are in the form of microcapillary reactors which are formed by two openings in the layer and a connection between these openings, said connection being in contact with the substrate surface.

38. System according to claim 29, wherein:

the layer applied to the substrate consists of a hydrophobic material and has a thickness of not more than 20 $\mu$m; and the individual disjunct regions of the substrate which are not covered by the layer are surrounded by one or more webs, said web or webs each being surrounded by a trench-like depression which extends or extend around the web.

39. System of claim 29, wherein the sensors comprise optical detection sensors.

40. System of claim 29, wherein the sensors comprise electrical detection sensors.

41. System of claim 29, wherein the sensors comprise chemical detection sensor.

42. Method of fabricating a detection system for detecting various analytes in one sample or for detecting one analyte in a multiplicity of samples, comprising a planar or essentially planar substrate surface and, arranged on said surface, arrays of analyte-binding capturing molecules, characterized by the following steps:

(a) providing a planar or essentially planar substrate with sensors for the chemical, optical or electrical detection of the analytes which are arranged directly on or in the surface of the substrate, (b) applying a layer to the substrate, said layer being either already micropatterned or applying a continuous layer to the substrate and micropatterning the layer, in each case in such a way that disjunct regions of the substrate, on or in whose surface sensors are arranged, are not covered by the layer, where layer and substrate are sealingly joined to one another at least around the uncovered regions, (c) bringing at least part of the uncovered regions into contact with at least one liquid which contains capturing molecules, in such a way that the capturing molecules are capable of adhering to the substrate surface and/or to the surface of the sensors or to bind thereto, (d) removing the non-adhering constituents of the liquid.

43. Method of claim 42, wherein the sensors comprise optical detection sensors.

44. Method of claim 42, wherein the sensors comprise electrical detection sensors.

45. Method of claim 42, wherein the sensors comprise chemical detection sensor.

* * * * *